United States Patent [19]

Krause et al.

[11] Patent Number: 5,545,124
[45] Date of Patent: Aug. 13, 1996

[54] METHOD FOR ALLEVIATING THE SENSATION OF PAIN

[75] Inventors: Hartmut Krause, Erlangen; Georg P. Dahmen; Ludwig Meiss, both of Hamburg, all of Germany

[73] Assignee: Siemens Aktiengesellschaft, Munich, Germany

[21] Appl. No.: 238,464

[22] Filed: May 5, 1994

[30] Foreign Application Priority Data

May 7, 1993 [DE] Germany .......................... 43 15 282.1

[51] Int. Cl.⁶ .................................................. A61B 17/00
[52] U.S. Cl. ................................................... 601/2
[58] Field of Search ........................ 601/2–4; 128/660.03

[56] References Cited

U.S. PATENT DOCUMENTS 3,499,437  3/1970  Balamuth .
3,942,531  3/1976  Hoff et al. .
4,526,168  7/1985  Hassler et al. .
4,674,505  6/1987  Pauli et al. .
4,697,588  10/1987  Reichenberger .
4,928,672  5/1990  Grasser et al. .
5,050,587  9/1991  Sagara et al. ................................ 601/2
5,172,692  12/1992  Kulow et al. ................................ 601/2
5,374,236  12/1994  Hassler ....................................... 601/2

FOREIGN PATENT DOCUMENTS 3038445  5/1992  Germany .

Primary Examiner—Ruth S. Smith
Attorney, Agent, or Firm—Hill, Steadman & Simpson, A Professional Corporation

[57] ABSTRACT

A method for alleviating the sensation of pain, particularly pain arising from, or sensed in, bone-proximate soft tissue regions, includes the step of charging the painful region with acoustic shockwaves.

24 Claims, 2 Drawing Sheets

# 5,545,124

METHOD FOR ALLEVIATING THE SENSATION OF PAIN

BACKGROUND OF THE INVENTION

1. Field of the Invention

The present invention is directed to a method for alleviating, i.e., ease or even eliminate, the sensation of pain, particularly pain arising from, or sensed in, bone-proximate soft tissue regions.

2. Description of the Prior Art

Pain relieving techniques are of significance in view of the large number of patients which suffer pain of a wide variety of types. The intake or administration of analgesics represents a considerable burden on the metabolism of the patient, particularly if a long-term intake or administration regimen is necessary. In many instances, the analgesic must be administered with increasingly larger doses, as the duration of the treatment regimen increases, in order to maintain alleviation of pain. Moreover, many patients have analgesic intolerance, or an allergy which prevents the administration of certain types of analgesics.

Pain arising in the bone-proximate soft tissue region is of special significance. Such pain can occur in the entire body. The past histories, i.e., the etiologies or pathogenies of pain arising in these soft tissue regions are not uniform.

Known therapy procedures are directed at the removal of the painful region and/or partial immobilization or enervation, i.e., severing the relevant nerve(s), of the affected region by surgical measures.

Temporary analgesia can also be achieved by the infiltration, i.e., injection, of local anesthetics, with and without the additional infiltration of corticosteroids.

Physical therapy is another known techniques which attempts to produce anodynia, i.e., an anodyne state.

In the case of extremely severe pain, it is also known to attempt to achieve a anodynia by irradiation with x-rays or gamma-rays.

Despite the employment of the above techniques, individually or in combination, some patients still experience pain which cannot be alleviated.

SUMMARY OF THE INVENTION

It is an object of the present invention to provide a method for alleviating pain which can at least partially or temporarily alleviate pain and which, in particular, is suitable for the treatment of pain arising in or felt in the bone-proximate soft tissue regions.

The above object is achieved in accordance with the principles of the present invention in a method for producing anodynia in a painful region which comprises the step of charging the painful region with acoustic pressure pulses. The fact that pain can be alleviated or eliminated by charging the situs of the pain with acoustic pressure pulses is surprising, because normally sensations of pain are produced by the pressure pulses in known therapy procedures (for other purposes), which involve the application of acoustic pressure pulses to a patient, such as lithotripsy. A theory for explaining this surprising result is that temporary changes in the respective cell membranes of cells which are subjected to pressure pulses result in a temporary blockage of the normal function of the cell membrane of serving as a transmitter or conduit between the interior of the cell and the exterior. This is particularly noticeable in the case of nerve cells, because their function is dependent on the function of the cell membrane. It is theorized that a "flood" of irritation, i.e., stimulation, occurs as a consequence of the application of pressure pulses, due to an overload of the nociceptors, or of the nociceptive nerve fibers. This flooding with irritation results in an inhibition of the forwarding of subsequent pulses. A particular advantage of the method of the invention is that no serious side-effects occur in conjunction with the method.

The painful region which is subjected to the pressure pulses need not necessarily have any pathological characteristics associated therewith, other than being a source of pain. The tissue subjected to the pressure pulses, therefore, need not be damaged or abnormal tissue. In other words, the pressure pulses may be directed at tissue which has the appearance and characteristics of "healthy" tissue, although the tissue may exhibit characteristics typical of pain sites, such as inflammation.

In a preferred embodiment of the method the pressure pulses are focused. It is thus possible to limit the treatment to that body region which is the point of origin of the pain.

The method is particularly effective when the pressure pulses are in the form of acoustic shockwaves. As used herein, the term "shockwaves" means positive acoustic pressure pulses having an extremely steep leading edge. The employment of shockwaves makes it possible to introduce the necessary acoustic energy into the body of the patient without a harmful overheating of the treated body regions. Previous tests have shown that energy densities on the order of magnitude of 0.05 through 0.6 $mJ/mm^2$ are expedient. The peak pressures of the acoustic pressure pulses preferably are on the order of magnitude of 50 through 700 bar. The pressure pulses usually have a so-called therapeutic region, or effective region, within which their intensity is adequate in order to produce a desired therapeutic effect. One therefore preferably proceeds by first locating and localizing the painful region, i.e., referencing the painful region with respect to an anatomical structure. This can be undertaken by means of ultrasound and/or x-ray locating, and the therapeutic region of the acoustic pressure pulses (shockwaves) is then brought into coincidence with the localized painful region.

An optimum alignment of the therapeutic region and the painful region relative to each other is achieved by obtaining feedback from the patient communicating with attending personnel so that the region wherein the maximum pain occurs is made to be coincident with the therapeutic region.

Preferably, the pressure pulses are generated by means of an electromagnetic shockwave generator, because the intensity, i.e., the energy density or peak pressure of the pressure pulses, which can be achieved by such shockwave generators can be well-regulated.

As a rule, one will proceed in the treatment according to the inventive method by administering a plurality of pressure pulses in a sequence. The intensity of the successive pressure pulses may be increased. Preferably the intensity is increased gradually and with an increasing number of pressure pulses during the sequence of pressure pulses. It is also expedient to increase the repetition rate of the pressure pulses, such increase also preferably occurring gradually during the application of the sequence of pressure pulses.

As a rule, more than one treatment will be necessary, with the charging of the painful region with pressure pulses preferably ensuing on successive days during a treatment phase which extends over a plurality of treatment days. Preferably the duration of the treatment phase is not substantially less than one week.

Similar to the expedient of increasing the intensity of the pressure pulses during a treatment, it is also recommended to increase the intensity of the pressure pulses from treatment day-to-treatment day during a treatment phase. If the treatment days do not immediately follow one another, however, preferably the treatment which is administered on the first day following a treatment interruption is begun employing pressure pulses having an intensity which is reduced in comparison to the intensity of the pressure pulses which were administered on the most recent preceding treatment day.

The duration of the freedom from or alleviation of pain experienced by the patient can be lengthened by the charging the painful region with pressure pulses in successive treatment phases.

The number of pressure pulses with which the painful region is sequentially charged should not fall significantly below 50 pulses, since a longer-lasting freedom from or alleviation of pain can otherwise not be expected. As a rule, an effective treatment will include the application of a plurality of pulses in sequence with the number of pulses not being significantly less than 1200 pulses. According to prior experience, it is not meaningful to apply a plurality of pressure pulses in sequence which significantly exceeds 3000 pulses, since the effectiveness of the treatment can no longer be expected to increase with such a high number of pulses.

In instances wherein the painful region is substantially larger than the therapeutic region of the pressure pulses, the method can be supplemented by displacing the painful region and the therapeutic region of the pressure pulses relative to each other so that different portions of the painful region are successively charged with pressure pulses.

Following the charging of the painful region with acoustic pressure pulses, the treated region can be cooled.

The following conditions have been treated with pressure pulses in the form of shockwaves for alleviating the sensation of pain in accordance with the inventive method: painful restrictions of movement at the shoulder due to tendinosis calcanea, tendinosis calcanea or impingement syndrome without restriction of movement, epikondylopathia humeri lateralis (tennis elbow), epikondylopathia humeri medialis (golfer elbow), pains in the region of the trapezius muscles, pains arising in the lumbar paravertebrae, pain arising in the region of a slack endoprosthesis, gonarthrosis, i.e., degenerative condition of the knee, pains in the region of the tuber ossis ischii, pains in the region of the trochanter major and of the proximal femur, and pains arising from a Haglund tendon (exostosis of the edge of the tuber calcanei) which was multiply operated upon.

The above enumeration is only for the purpose of example; pains caused by other conditions can also be treated in accordance with the principles of the inventive method.

DESCRIPTION OF THE PREFERRED EMBODIMENTS

Figure 1:
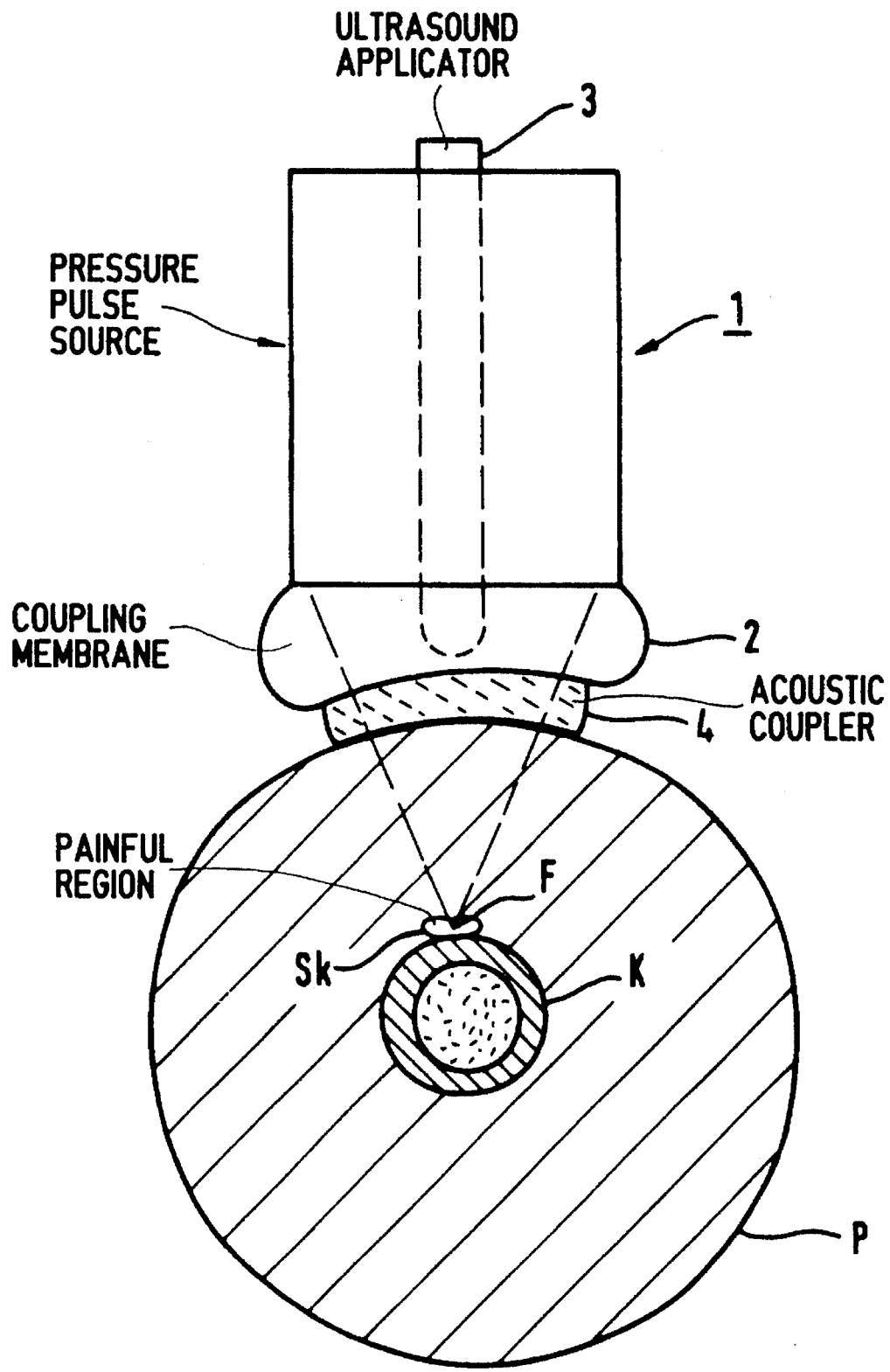
FIG. 1 is a schematic view of a region of a patient, in section, with an acoustic pressure pulse source applied thereto for conducting treatment in accordance with the principles of the inventive method.

A patient P is shown in FIG. 1, to whom an acoustic pressure pulse source 1 is applied. The acoustic pressure pulse source 1 emits focused acoustic pressure pulses in the form of shockwaves. Using an ultrasound locating system, which has an ultrasound applicator 3 integrated in the pressure pulse source 1, the pressure pulse source 1 is applied to the body surface of the patient 3 by means of an elastic coupling membrane 2 so that a painful region SK located within the body of the patient P can be treated with the shockwaves. The patient P is treated in a treatment phase consisting of a plurality of, for example 5 through 30, treatments or sessions. In each session, preferably 1200 through 3000 shockwaves (but not fewer than 50 shockwaves) are sequentially administered. The peak pressure of the shockwaves preferably is on the order of magnitude of 50 bar. The energy density of the shockwaves preferably is on the order of magnitude of 0.1 $mJ/mm^2$. In order to adapt the treatment to a given case, however, peak pressures in a range of 20 through 700 bar and/or energy densities in a range of 0.05 through 0.6 $mJ/mm^2$ can be employed. The peak pressure and the energy density of the shockwaves can be set within these ranges. The intensity of the shockwaves is increased from treatment to treatment during the individual treatments. The repetition rate of the shockwaves is also increased during a treatment, such as to a maximum of approximately 4 Hz. A reduced repetition rate which is comfortable for the patient, for example, 0.2 Hz, can be selected at the beginning of a particular treatment.

The structure of suitable electromagnetic pulse sources which can be employed for conducting the inventive method is disclosed for example, in U.S. Pat. No. 4,697,588, U.S. Pat. No. 4,674,505 and European Application 0 301 360.

The structure of the apparatus for conducting the method of the invention, i.e., the pressure pulse source 1 shown in FIG. 1, is explained in greater detail below with reference to FIG. 2 as an example of a suitable structure.

The pressure pulse source I may include a substantially cylindrical, tubular housing 5, a shockwave generator assembly generally referenced 6 being disposed in the region of the one end of the housing 5, serving as a pressure pulse generator. The housing 5 of the pressure pulse source 1, which is rotationally symmetrical relative to its center axis M, has an open end which is covered by the flexible coupling membrane 2. The pressure pulse source I is pressed by means of the coupling membrane 2 against the body of the patient P for acoustic coupling in the manner shown in FIG. 1. The housing 5 is filled with an acoustic propagation medium, such as water, for the shockwaves emanating from the shockwave generator assembly 6.

An acoustic positive lens 7 is disposed in front of the shockwave generator 6, serving the purpose of focusing the planar shockwaves which emanate from the shockwave generator assembly 6. These shockwaves then converge, as indicated with dashed lines in FIGS. 1 and 2, in a therapeutic region (or effective region) FZ (also indicated with dashed lines), having a center which theoretically corresponds to the focus F of the positive lens 7 lying on the center axis M. The shockwave generator assembly 6 and the positive lens 7 are provided with respective central openings which are in registry, through which a tube accepting applicator 3 extends. This allows ultrasound B-images of a slice of the body of the patient P, which contains the center axis M and the corresponding portion of the therapeutic region FZ of the shockwaves, to be produced by imaging electronic 8.

After localization of the painful region SK, and a positional referencing thereof relative to an anatomical structure, such as to a bone K in the case of FIG. 1, it is possible in a known manner, using the ultrasound locating system formed by the ultrasound applicator 3, the imaging electronics 8 and a monitor 9, and/or an x-ray locating system (not separately shown) to spatially adjust the position of the pressure pulse source 1. This is accomplished employing a schematically indicated adjustment unit 17, having control elements 18, 19 and 20. The pressure pulse source 1 is aligned, relative to the stationary body of the patient P, so that the therapeutic region FZ of the shockwaves lies within the painful region SK, as shown in FIG. 1. This can occur, for example, with the assistance of a mark F, identifying the position of the center F of the therapeutic region FZ, which is mixed in a known manner into the ultrasound B-image also displayed on the monitor 9.

Figure 2:
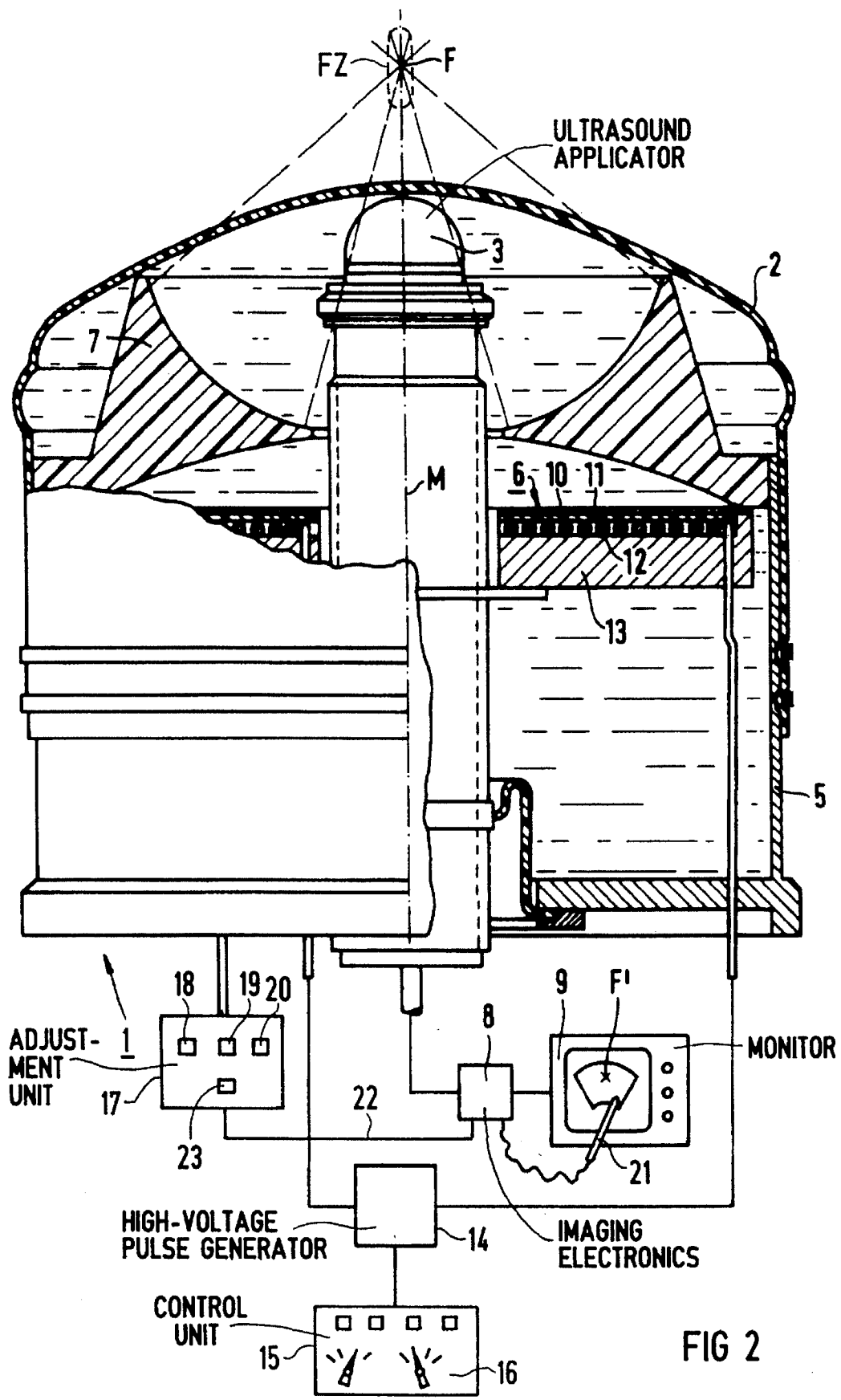
FIG. 2 is a schematic view, in longitudinal section, through the pressure pulse source shown in FIG. 1.

The edge or marginal rays of the shockwaves are indicated with dashed lines in FIGS. 1 and 2.

Other types of adjustment, for example adjustment of only the patient P or adjustment of both the patient P and the pressure pulse source 1 are possible, in order to align the painful region SK and the therapeutic region FZ in the required manner.

If the painful region SK is larger than the therapeutic region FZ, the painful region SK and the therapeutic FZ must be gradually displaced relative to each other, for example, using the adjustment unit 17, so that the entire painful region SK is eventually charged with shockwaves in the required manner. To this end, a light pen 21 can be provided with which the boundaries of the painful region SK can be marked on the image thereof on the picture screen of the monitor 9. Corresponding signals are supplied to the adjustment unit 17 from the imaging electronics 8 via a line 22. When a further control element 23 of the adjustment unit 17 is activated, the above-described relative displacement of the painful region SK and the therapeutic region FZ ensues automatically. This displacement can alternatively be manually controlled using the control elements 18 through 20.

As further shown in FIG. 2, the shockwave generator assembly 6 includes a planar membrane 10 containing an electrically conductive material, for example copper or aluminum disposed such that one side thereof is adjacent the propagation medium contained in the housing 5. The other side of the membrane 10 faces a helically wound flat coil 12, with an insulating foil 11 disposed between the membrane 10 and the coil 12. The coil 12 is applied to a coil carrier 13 by, for example, gluing. The flat coil 12 is electrically connectable to a high-voltage pulse generator 14 via two terminals, with which the flat coil 12 can be charged with high-voltage pulses having a high current intensity (in the kV and kA range). The high-voltage pulse generator 14 is designed so that the intensity of the shockwaves, the repetition rate of the shockwaves, the number of the shockwaves per sequence, and the rates of increase of the intensity and of the repetition rate within a sequence can be set. For this purpose, a control unit 15 having a control panel 16 is provided, which is connected to the high-voltage generator 14 and permits the aforementioned parameters to be set in any desired combination.

When the flat coil 12 is charged with a high-voltage pulse from the pulse generator 14, the membrane 10 is caused to be rapidly repelled away from the flat coil 12. As a result, a shockwave is formed in the propagation medium situated in the housing 5, and this shockwave is focused by the acoustic positive lens 7.

As indicated with dashed lines in FIG. 1, an additional acoustic coupler 4, such as a water bag or a hydrogel disk, can be disposed between the body surface of the patient P and the coupling membrane 2. In the case of a painful region which is situated close to the body surface of the patient P, the acoustic coupler 4 can serve the purpose of enabling coupling of the pressure pulse source I to such a region, and can also serve to reduce the intensity of the shockwaves below the minimally adjustable value. In the latter case, the acoustic coupler 4 can consist of, or contain, an attenuating medium such as rubber or caster oil.

Although it is of particular advantage to employ electromagnetic pressure pulses sources of the type described above, since these can be controlled with a high degree of precision and in a manner which affords a wide range of parameter selection, other types of pressure pulse sources, for example, piezoelectric sources as described in U.S. Pat. No. 4,526,168, electrohydraulic sources as described in German PS 23 51 247, or magnetostrictive pressure pulse sources can be employed. Moreover, the pressure pulse source which is employed need not necessarily be a shockwave source. Acoustic pressure pulse sources which generate acoustic pressure pulses which are not classified as shockwaves can alternatively be employed. For example, some types of patients may respond best to treatment with acoustic pressure pulses exhibiting a negative pressure (so-called tractive or rarefaction pulses), in which case a suitable source for generating these types of negative pressure pulses will be employed.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for alleviating the sensation of pain in a body region in which said sensation of pain originates, comprising the step of:

charging said body region with acoustic shockwaves and thereby causing said sensation of pain in said body region to be reduced after said charging.

2. A method as claimed in claim 1 comprising the additional step of focusing said shockwaves.

3. A method as claimed in claim 1 comprising the additional step of generating said acoustic shockwaves with an electromagnetic shockwave source.

4. A method as claimed in claim 1 wherein the step of charging said painful region with acoustic shockwaves is further defined by charging said painful region with acoustic shockwaves having a therapeutic region, and comprising the additional steps of:

identifying the location of said painful region in a patient; and orienting said therapeutic region and said painful region relative to each other so that said painful region lies in said therapeutic region of said shockwaves.

5. A method as claimed in claim 1 wherein said painful region has a region at which the pain is a maximum, wherein the step of charging said painful region with acoustic shockwaves is further defined by charging said painful region with acoustic shockwaves having a therapeutic region, and comprising the additional step of:

orienting said therapeutic region and said painful region relative to each other so that said region wherein the pain is a maximum lies in said therapeutic region of said shockwaves.

6. A method as claimed in claim 1 wherein the step of charging said painful region with acoustic shockwaves is further defined by the steps of:

charging said painful region with a plurality of said shockwaves in sequence, each shockwaves having an intensity; and increasing the intensity of successive pressure pulses during said sequence.

7. A method as claimed in claim 1 wherein the step of charging said painful region with acoustic pressure pulses is further defined by charging said painful region with a plurality of said acoustic shockwaves in sequence at a repetition rate, and increasing said repetition rate of successive shockwaves during said sequence.

8. A method as claimed in claim 1 wherein the step of charging said painful region with acoustic shockwaves is further defined by charging said painful region with acoustic shockwaves at a repetition rate not exceeding 4 Hz.

9. A method as claimed in claim 1 comprising the additional step of:
conducting said shockwaves through an acoustic damping member before said shockwaves reach said painful region.

10. A method as claimed in claim 1 wherein the step of charging said painful region with acoustic shockwaves further defined by charging said painful region with acoustic over a treatment phase comprised of a plurality of treatment days and having a duration which does not substantially fall below one week.

11. A method as claimed in claim 1 wherein the step of charging said painful region with acoustic pressure pulses is further defined by charging said painful region with acoustic shockwaves during a treatment phase comprising a plurality of treatment days and having a duration which does not substantially exceed six weeks.

12. A method as claimed in claim 1 wherein the step of charging said painful region with acoustic shockwaves is further defined by charging said painful region with acoustic shockwaves during a treatment phase comprising a plurality of treatment days, said shockwaves having an intensity, and increasing the intensity of said shockwaves from treatment day to treatment day.

13. A method as claimed in claim 1 wherein the step of charging said painful region with acoustic shockwaves is further defined by charging said painful region with acoustic shockwaves in successive treatment phases.

14. A method as claimed in claim 1 wherein the step of charging said painful region with acoustic shockwaves is further defined by charging said painful region with a sequence consisting of a plurality of said shockwaves which is not significantly less than 50.

15. A method as claimed in claim 1 wherein the step of charging said painful region with acoustic shockwaves is further defined by charging said painful region with a sequence consisting of a plurality of said shockwaves which is not significantly less than 1200.

16. A method as claimed in claim 1 wherein the step of charging said painful region with acoustic shockwaves is further defined by charging said painful region with a sequence consisting of a plurality of said shockwaves which does not significantly exceed 3000.

17. A method as claimed in claim 1 wherein the step of charging said painful region with acoustic shockwaves is further defined by charging said painful region with acoustic shockwaves having a therapeutic region, and comprising the additional step of displacing said painful region and said therapeutic region relative to each other for successively charging different portions of said painful region with said shockwaves.

18. A method as claimed in claim 17 comprising the additional step of:
selecting said bone-proximate soft tissue region from the group consisting of tissue regions exhibiting degenerative, inflammatory or tumorous conditions.

19. A method as claimed in claim 1 comprising the additional step of cooling said painful region after charging said painful region with shockwaves.

20. A method as claimed in claim 19 wherein the step of charging said painful region with acoustic shockwaves is further defined by charging a painful region in the region of an endoprosthesis.

21. A method as claimed in claim 1 wherein the step of charging said painful region with acoustic shockwaves is further defined by charging a bone-proximate soft tissue region with said acoustic shockwaves.

22. A method as claimed in claim 1 wherein the step of charging said painful region is further defined by charging the painful region of a condition of the group consisting of:
tendinosis calcanea, epikondylopathia humeri lateralis, epikondylopathia humeri medialis, pains in the region of the trapezius muscle, pains arising in the lumbar paravertebrae, gonarthrosis, pains in the region of the tuber ossis ischii, pains in the region of the trochanter major, pains in the region of the proximal femur pains arising from a Haglund tendon.

23. A method for alleviating the sensation of pain in a body region in which said sensation of pain originates, comprising the step of;
charging said body region with acoustic pressure pulses each having an energy density in the range of 0.05 through 0.6 mJ/mm$^2$ and thereby causing said sensation of pain in said body region to be reduced after said charging.

24. A method for alleviating the sensation of pain in a body region in which said sensation of pain originates, comprising the step of;
charging said body region with acoustic pressure pulses with each pressure pulse having an order of magnitude in the range of 50 through 700 bar and thereby causing said sensation of pain in said body region to be reduced after said charging.

* * * * *